(12) United States Patent
Brusca et al.

(10) Patent No.: US 8,212,118 B1
(45) Date of Patent: Jul. 3, 2012

(54) WATERMELON POLLENIZER SP-6

(75) Inventors: James Brusca, Woodland, CA (US); Xingping Zhang, Woodland, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/366,542

(22) Filed: Feb. 6, 2012

(51) Int. Cl.
- *A01H 5/00* (2006.01)
- *A01H 5/10* (2006.01)
- *A01H 1/00* (2006.01)
- *A01G 1/06* (2006.01)
- *A01G 1/00* (2006.01)

(52) U.S. Cl. .............................. 800/308; 800/260; 47/6

(58) Field of Classification Search .................... 800/308
See application file for complete search history.

(56) References Cited

U.S. PATENT DOCUMENTS

| | | | |
|---|---|---|---|
| 5,007,198 | A | 4/1991 | Gray et al. |
| 6,355,865 | B1 | 3/2002 | Elmstorm |
| 6,759,576 | B2 | 7/2004 | Zhang et al. |
| 7,071,374 | B2 | 7/2006 | Zhang et al. |
| 7,528,298 | B2 | 5/2009 | Zhang et al. |
| 7,550,652 | B2 | 6/2009 | Zhang |
| 2003/0121075 | A1 | 6/2003 | Barham |
| 2003/0163852 | A1 | 8/2003 | Barham et al. |
| 2009/0133141 | A1 | 5/2009 | Zhang et al. |
| 2011/0185443 | A1* | 7/2011 | Zhang et al. ................. 800/260 |

FOREIGN PATENT DOCUMENTS

| | | |
|---|---|---|
| WO | WO 00/70933 | 11/2000 |

OTHER PUBLICATIONS

Buttrose et al., Ann. Bot., 1978, 42, pp. 599-608.
Crall et al., HortScience, 1994, 29, 6, pp. 707-708.
Min et al., Acta Genetica Sinica, 2000, 27, 10, pp. 902-910.
Gusmini et al., Crop Sci., Jan.-Feb. 2005, 45, pp. 141-146.
Hegde, J. Agronomy and Crop Science, 1988, 160, pp. 296-302.
Hochmuth et al., "Cultural Management" in Watermelons: Characteristics, Production, and Marketing (Virginia, ASHS Press, 2001), pp. 78-97.
Kano, Journal of Horticultural Science and Biotechnology, 2004, 79, 1, pp. 142-145.
Karchi et al., Cucurbit Genetics Cooperative Report, 1983, 6, pp. 59-61.
Kenny et al., American Society for Horticultural Science, 1941, 38, pp. 537-540.
Known-You Seed Co., Ltd., (Kaohsiung, Taiwan), [catalog], 1991/92, pp. 22.
Known-You Seed Co., Ltd., (Kaohsiung, Taiwan), [catalog], 1994, pp. 2.
Maynard et al., Acta Horticulture, 1992, 318, pp. 169-178.
NeSmith et al., HortScience, Feb. 2001, 36, 1, pp. 60-61.
Poehlman et al., "Quantitative Inheritance," In Breeding Field Crops, 4th ed., Iowa State University Press, Ames, 1995, pp. 71.
Poole, The Journal of Heredity, 1944, 35, pp. 122-128.
Porter, Hilgardia, 1937, 10, 12, pp. 489-509.
Rhodes et al., Cucurbit Genetics Cooperative Report, 1999, 22, pp. 61-77.
Scott et al., HortScience, Sep. 1990, 25, 9, pp. 1075.
Sugiyama et al., J. Japan. Soc. Hort. Sci., 1999, 68, 1, pp. 108-116.
Sundstrom et al., J. Amer. Soc. Hort. Sci., 1983, 108, 5, pp. 879-881.
Susin et al., Euphytica, 1997, 93, pp. 369-373.
Watermelon (and Stockmelon, Pie Melon, or Citron Melon) in Insect Pollination of Cultivated Crop Plants by S.E. McGregor, USDA, originally published 1976. [online].
Wagner Force Instruments, [catalogue] [online]. [Internet: <URL: http://www.wagnerinstruments.com/] retrieved Jan. 13, 2004.
Wagner Force Measurement Instruments, [Wagner Fruit Test online manual]. [Internet: <URL: http://www.wagnerinstruments/manuals/ftmanual.pdf] retrieved Jan. 13, 2004.
Wolf et al., HortScience, 1999, 34, 5, pp. 860-863.
Davis et al., Watermelon resistance to powdery mildew race 1 and race 2. In: Cucurbitaceae 2006, Holmes, ed. Universal Press, Raleigh, NC pp. 412-420.
Davis et al., 2001, Cucurbit Genet. Coop. Rep., 24, pp. 42-48.
Davis et al., 2007, J. Amer. Soc. Hort. Sci., 132, pp. 790-795.
Thomas et al., 2005, HortSci., 40, pp. 154-156.

* cited by examiner

*Primary Examiner* — Anne Kubelik

(74) *Attorney, Agent, or Firm* — S. Matthew Edwards

(57) ABSTRACT

The present invention provides a novel watermelon variety designated SP-6, and method for pollinating seedless watermelon plants. The present invention also provides methods for producing triploid, seedless watermelon fruit.

29 Claims, No Drawings

WATERMELON POLLENIZER SP-6

FIELD OF THE INVENTION

This invention is in the field of watermelon breeding, specifically relating to a watermelon variety. In one aspect, the watermelon variety is used to pollinate triploid watermelon plants for the commercial production of seedless watermelon fruit.

BACKGROUND OF THE INVENTION

Watermelon is an important specialty crop that is common in all major agriculture production areas and accounts for 6.8% of the world area devoted to vegetable and melon crops (Derived from data supplied by United Nations Food and Agriculture Organization, FAOStat (http://faostat.fao.org/site/567/default.aspx). There were 8,900,300 of acres of watermelon grown in the world and 150,700 acres of watermelons grown in the United States in 2007. The United States is the fifth largest watermelon production country in the world. Asia is by far the most important watermelon production site with nearly ⅔ of the world area and slightly over ⅔ of the world production (United Nations, Food and Agriculture Organization, FAOStat (February 2008)). There were 125,550 acres of watermelon planted in the USA, accounting 7.25% of US vegetable acreage, with a total production of 39.551 million cwt and farm value of $492,446,000 in 2008 (USDA, NASS, Vegetables Annual Summary (2004-2008)). Majority of the watermelon acreage in the USA are seedless watermelon. California was the leading state in watermelon farm gate value, exceeded $72.981 million in 2004, due to higher percentage of triploid seedless watermelon grown in California. Seedless watermelon receives above the average price for seeded watermelons in the market. Triploid seedless watermelon also produces higher yields than the diploid seeded watermelons. The significantly increased watermelon productivity and farm value, as well as decreased production acreage, in the USA since the mid-1990s are the result of using triploid seedless watermelon varieties in commercial production.

The goal of plant breeding is to combine in a single variety or hybrid various desirable traits. Desirable traits may include resistance to diseases and insects, tolerance to heat and drought, reducing the time to crop maturity, greater yield, and better agronomic and produce quality. With mechanical harvesting of many crops, uniformity of plant characteristics such as germination and establishment, growth rate and maturity, are important. Other desired traits may include particular nutrient content, color, fruit shape, as well as taste characteristics.

As with many different plants, a watermelon plant contains a fruit part and a plant part. Each part contains different traits that are desired by consumers and/or growers, including such traits as flavor, texture, disease resistance, and appearance traits such as shape and color. The seedless trait in the watermelon fruit is highly desired by consumers. For production of seedless watermelon, optimum pollination characteristics of the pollenizer plant (plant provides viable pollen for the triploid plant) are desired.

Seedless watermelon plants are triploid and must be pollinated by the pollen of diploid watermelon plants. To provide adequate pollenization of seedless watermelon plants, it is current practice to plant diploid pollenizer plants over approximately 25-33% of the field surface. The remaining portion of the field is planted with the triploid plants. Thus, to maximize the value of the crop in the field, growers use high yield marketable diploid watermelon varieties, which ultimately compete with the triploid seedless varieties for sun, nutrients, and space. The present invention recognizes the need to increase the pollenizing capacity of diploid watermelon plants in order to decrease the ratio of diploid to triploid plants in the field, thereby increasing the yield of the seedless watermelon. The present invention further recognizes the need for phenotypic characteristics of the diploid pollenizer plants, which permit these diploids to be planted in close proximity to the triploid plants and to share the field surface with the triploid plants, thereby effectively decreasing the surface area of the field required for the diploid pollenizers of the invention. The present invention also further recognizes the need for pollenizer plants with improved resistance to diseases.

SUMMARY OF THE INVENTION

The present invention provides a novel watermelon variety designated SP-6. The present invention also provides methods for pollinating seedless watermelon plants using plants of watermelon variety SP-6. The present invention also provides methods to produce triploid seedless watermelon fruits and uses of the novel watermelon variety to improve current methods of commercial production of seedless watermelon and to increase the yield of seedless watermelon fruit.

According to the invention, watermelon variety SP-6 is resistant to Zucchini Yellow Mosaic Virus, Fusarium wilt race 1 (Fon 1), Powdery Mildew race 1 and to Anthracnose race 1 (Col 1), and intermediate resistant to Fusarium wilt race 2 (Fon 2). In another aspect of the invention, watermelon variety SP-6 is a diploid watermelon inbred line.

According to the invention, watermelon variety SP-6 has a high number of thin (lacy) branches. The openness of the branched or lacy vine results, in part, from the distinct small and non-overlapping, deep lobed leaves. The lacy branches and small, non-overlapping, deep lobed leaves of the invention provide more access of bees to the flowers of both the pollenizer and the triploid plant, thereby enhancing transfer of the pollen from plants of watermelon variety SP-6 to the female flowers of the triploid watermelon plants. A second advantage of small leaves characterized by deep, non-overlapping lobes is that more sunlight is able to penetrate to adjacent triploid plants. The third advantage of small leaves characterized by deep, non-overlapping lobes is that these leaves take up less field area.

Also according to the present invention, watermelon variety SP-6 comprises small fruits with brittle rinds. The small fruits with brittle rinds reduce the load to the plant and allow the plant to continue flowering for extended periods of time. The long flowering duration of the plants of watermelon variety SP-6 results in increased fruit set and yield of seedless watermelon.

The fruits of watermelon variety SP-6 weigh approximately in the range of 1.5 to 3.5 kg, especially approximately 2 kg. The rind of the fruits of watermelon variety SP-6 is brittle. In one embodiment, the rind of the fruits of watermelon variety SP-6 breaks under a pressure in the range of about 800 g to about 1,500 g when a Wagner Fruit Test™ FT11 with a 2 mm tip is used.

The skin color of the fruits of watermelon variety SP-6 is light green. In one embodiment, it is different from the skin color of the fruits of most commercially grown seeds watermelon varieties.

In one embodiment, the present invention discloses a method for producing triploid, seedless watermelon fruit comprising the steps of inter-planting a seed or a plant of watermelon variety SP-6 and seed or plants of triploid watermelon plants in a field; and allowing pollination of said triploid watermelon plants by pollen of said plant of watermelon variety SP-6 to obtain triploid, seedless watermelon fruit. In one embodiment, the method further comprises harvesting seedless watermelon fruit from triploid plants.

The present invention also provides a method for interplanting plants of watermelon variety SP-6 amongst the triploid watermelon plants in a field. The invention also provides a method of increasing the yield of triploid seedless watermelon plants by plants of watermelon variety SP-6, wherein the fruit are not harvested for human consumption.

In one embodiment, the present invention discloses a method of producing seeds of watermelon variety SP-6 comprising growing a plant of watermelon variety SP-6; allowing pollination of said plants, for example open-pollination of said plants in an isolated plot/field; and harvesting seeds from said plants. In one embodiment, the method further comprises washing and drying said seed.

In one embodiment, the present invention discloses a method of vegetative propagating watermelon variety SP-6 comprising collecting shoot tissue of a plant of watermelon variety SP-6; cultivating said tissue to obtain proliferated shoots; rooting said proliferated shoots to obtain rooted plantlets. In one embodiment, the method further comprises growing plants from said rooted plantlets. In one embodiment, the method further comprises harvesting seeds from said plants. In one embodiment, the method further comprises washing and drying said seed.

DETAILED DESCRIPTION OF THE INVENTION

Development of Seedless Watermelons

Triploid watermelons are created by crossing a tetraploid (4X) female line with diploid (2X) male line. The resulting triploid (3X) watermelon seed are planted in a field with diploid watermelon pollenizers. The resulting fruit of the triploid watermelon are seedless.

To create a tetraploid female watermelon line, it is known in the art to use chemicals that alter mitosis of a diploid inbred line so that doubled numbers of chromosomes are obtained in the somatic cells. For example, colchicine is a chemical that alters the mitotic spindle fibers of diploid cells resulting in a number of cells that are tetraploid. Similarly, oryzalin or other mitotic blocking dinitroaniline herbicide can be used for doubling chromosome (Zhang, 2004, U.S. Pat. No. 6,747,191, Inbred Tetraploid Watermelon Line 90-4194). The diploid line used to create a tetraploid is selected based on the traits desired for the tetraploid line. Traits that are desired for a tetraploid line may therefore first be introgressed into the diploid inbred lines that will be used to develop the tetraploid lines by breeding methods well known to those skilled in the art. Thus, the diploid and tetraploid parent lines are bred separately for the desired traits.

It usually requires at least two generations of self-pollination and selection to "fix" the 4X condition, after the colchicine treatment generation because, often, chromosomal aberrations are encountered that affect seed fertility, and must be eliminated. Once the stable tetraploid containing the desired characteristics is verified, it then can be used as a stable female parent for the production of the triploid hybrid. A stable diploid inbred is selected for use as the male parent. Methods for developing tetraploid plants are described in Kihara, H., 1951, Triploid Watermelons, *Proceedings of American Society for Horticultural Science* 58:217-230; and Eigsti, O. J., 1971, Seedless Triploids, HortScience 6, pgs. 1-2. A new tetraploid line can also be developed by crossing two or more existing tetraploid lines through conventional recombination breeding method and process (Walter R. Fehr, 1987, Principles of Cultivar Development, volume 1: Theory and Technique, pgs, 59-62. Macmillan Publishing Company, ISBN 0-02-949920-8.

The tetraploid female and diploid male are planted in a seed production field. The pollen of the diploid male parent is transferred to the female tetraploid flower by methods well known to those skilled in the art. The triploid seed that is produced is present in the resulting fruit and is planted to produce the triploid plants. The breeding of watermelon is further described in Mark Bassett (Editor), 1986, Breeding Vegetable Crops, AVI Publishing, ISBN 0-87055-499-9.

A triploid seedless watermelon is a true F1 hybrid between a tetraploid watermelon, as the female parent, and a diploid watermelon, as the male parent (Kihara, H.1951. Triploid Watermelons. *Proceedings of American Society for Horticultural Science* 58:217-230). The seedless condition in triploid watermelon is the result of the presence of three homologous sets of chromosome per somatic cell rather than the usual two. Cells with three sets of homologous chromosomes are said to be triploid and are designated as 3X. The triploid seedless watermelons have 33 chromosomes (2N=3X=33) in their somatic cells. The inability of the triploid zygote to produce normal viable gametes (pollen and egg cells) causes the absence of seeds in triploid fruits. Typically, seedless watermelons contain small edible white ovules, similar to those in immature cucumbers.

Adequate viable pollen supply from the diploid pollenizer watermelon is essential for the triploid female flowers to set and develop into regular seedless fruit. The female flowers of triploid watermelon will not set if they are not pollinated by viable pollen of diploid watermelon. (Maynard, D. N. (editor), 2001, *Watermelons: Characteristics, Production and Marketing*, ASHS Press, ISBN 0-9707546-1-2). The diploid watermelon grown in a field of triploid plants is referred to herein as the "pollenizer."

Development of Watermelon Variety SP-6

Watermelon SP-6 (also referred to herein as "SP-6") was developed as a pollenizer for triploid watermelon in the production of seedless fruit. SP-6 was developed at Syngenta Seeds' Research Stations in Woodland, Calif., Naples, Fla., and Khon Kaen, Thailand, as a result of traditional recombination breeding.

The breeding goal for SP-6 was to add resistance to Zucchini Yellow Mosaic Virus (ZYMV) to Syngenta watermelon variety SP-5 (U.S. patent Ser. No. 12/695,649 and PVP No. 2001000008). The following selection criteria were used for the development of watermelon variety SP-6:
1. Plant with more and thin (lacy) branches
2. Plant with small leaf and small deep leaf lobes
3. Plants with deep green foliage color
4. Plant flowers early and over a long period of time
5. Plant produces fruits with small size (<2 KG) and brittle rind (much easier to break compared to regular diploid and triploid watermelons)
6. Skin color different from currently commercial grown seedless watermelons
7. Plant with resistances to Fusarium wilt, Anthracnose, Powdery Mildew and Zucchini Yellow Mosaic Virus.
8. Yellow flesh with tan seed color.
9. Medium-large seed size.

The chronological description of the development of SP-6 is outlined in Table 1. The starting materials were Syngenta watermelon variety SP-5 (as described in U.S. Pat. No. 6,759, 576/No. 7071374/No. 7528298 and PVP No. 201000008) and watermelon Plant Introduction PI595203, also known as "Egun". PI595203 was classified as Zucchini Yellow Mosaic Virus resistant by Boyhan et. al. (Boyhan G, Norton J D, Jacobsen B J, Abrahams B R (1992) Evaluation of watermelon and related germplasm for resistance to Zucchini yellow mosaic virus. Plant Dis 76:251-252) and confirmed by Guner (Guner N (2004) Papaya ringspot virus watermelon strain and Zucchini yellow mosaic virus resistance in watermelon. PhD Dissertation, North Carolina State University, Raleigh, N.C., USA). PI595203 is the donor for virus resistance in SP-6.

In the summer of 2008, SP-5 was crossed with PI595203 to introduce resistance to Zucchini Yellow Mosaic Virus and the resulting F1 was selfed in the greenhouse in Woodland in the winter of 2009 to generate an F2 population. The resulting F2 population was sown in the greenhouse in the summer of 2009 and the F2 individuals were co-inoculated with ZYMV and PRSV. A surviving individual (plant 6) was transplanted into the greenhouse in Woodland and backcrossed to SP-5 to generate the BC1F1. The resulting BC1F1 was self pollinated in the greenhouse in the fall of 2009 to generate a BC population.

The resulting BC1F2 population was grown in the field in Khon Kaen, Thailand in the winter of 2010 and one single plant selection was made for plant architecture, plant health, fruit size, and the explosive rind character controlled by the e gene. This single plant was control self pollinated to generate a BC1F3 line.

The resulting BC1F3 line was indexed in the summer of 2010 for resistance to Fusarium race 2 and ZYMV. Both resistances were confirmed to be fixed. Simultaneously, the BC line was grown in Khon Kaen, Thailand and three single plant selections were made for plant type, fruit type, and seed color. These single plant selections were control pollinated to generate BC1F4 lines.

In the fall of 2010, these BC1F4 lines were indexed against Fusarium race 1, Fusarium race 2, Anthracnose race 1, Powdery Mildew, and Zucchini Yellow Mosaic Virus in the greenhouse in Woodland, Calif. Simultaneously, the three BC lines were grown in Khon Kaen, Thailand to phenotype for plant and fruit characteristics. Based on the Woodland greenhouse pathology indexing, one of the BC lines was confirmed to be fixed for resistance to Fusarium race 1, Fusarium race 2, Anthracnose race 1, Powdery Mildew, and segregating for resistance to Zucchini Yellow Mosaic Virus. This same BC was fixed for the desired plant and fruit characteristics. 7 single plants in this BC1F4 were control pollinated to generate BC1F5 lines.

The resulting 7 BC1F5 lines were indexed in the greenhouse in Woodland, Calif. against Fusarium race 2 and ZYMV in the spring of 2011. Simultaneously, the same 7 lines were grown in Khon Kaen, Thailand. A single BC1F5 line was selected based on the Woodland greenhouse Fusarium 2 and ZYMV resistance index results, and fruit and plant type from the plot in Khon Kaen, Thailand. 5 individuals in this selected line were self pollinated and carried forward to the BC1F6 generation.

In the summer of 2011, the 5 BC1F6 lines were screened in the Woodland greenhouse against Fusarium race 1, Fusarium race 2, Anthracnose race 1, Powdery Mildew, and ZYMV to confirm fixation of resistance. Simultaneously, the same generation BC1F6 lines were grown in the field in Woodland, Calif. and phenotyped for plant and fruit characteristics. Simultaneously, the same 5 BC1F6 lines were grown in Khon Kaen, Thailand, self-pollinated and phentoyped for plant and fruit characteristics. The BC1F6 line displaying the highest resistance levels based on the Woodland greenhouse screens and the most desirable plant and fruit characteristics based on the Woodland field and Khon Kaen field trials was self pollinated in Khon Kaen and bulk seed was harvested from the line. 44 plants of the BC1F7 line were grown in fall 2011 in Khon Kaen, Thailand for seed increase to produce BC1F8 seed. Simultaneously, this line was tested in Woodland, Calif. to confirm resistance against Fusarium race 1, Fusarium race 2, Anthracnose race 1, Powdery Mildew, and ZYMV. Simultaneously, the line was tested in the open field as a pollenizer variety for open field triploid (seedless) seedless watermelon production at Syngenta's Naples, Fla. research station and to confirm genetic stability and phenotypic uniformity.

Based on observations in the large number of plants in the summer of 2011 in Woodland, Calif. and in the fall of 2011 in Khon Kaen, Thailand and Naples, Fla., the SP-6 line is genetically stable and phenotypically uniform. No variants have been observed in the population of variety SP-6.

SP-6 is distinct from SP-5 in that it has tan seed color (versus the red of SP-5) and provides resistance to Zucchini Yellow Mosaic Virus (versus susceptibility in SP-5).

TABLE 1

Chronological Description of the Development of Diploid Watermelon Variety SP-6

| Year | Season | Location | Cross | Progeny | Purpose |
| --- | --- | --- | --- | --- | --- |
| 2008 | Summer | Woodland greenhouse | SP-5 × PI595203 | F1 | Add ZYMV resistance to SP-5 |
| 2009 | Winter | Woodland greenhouse | | F2 | Selfing to generate F2 population |
| 2009 | Summer | Woodland greenhouse | (SP-5 × PI595203) × SP-5 | BC1F1 | Screening of F2 population against ZYMV; Backcrossing of resistant F2 individual by SP-5 |
| 2009 | Fall | Woodland greenhouse | | BC1F2 | Selfing to generate BC1F2 population |
| 2010 | Winter | Khon Kaen, Thailand field; Woodland greenhouse | | BC1F3 | Select for plant type, fruit size, and rind explosiveness. |
| 2010 | Summer | Khon Kaen, Thailand field; Woodland greenhouse | | BC1F4 | Select for plant type, fruit type and seed color; Index for Fon 2 and ZYMV resistance |
| 2010 | Fall | Khon Kaen, Thailand field; Woodland greenhouse | | BC1F5 | Selection for plant and fruit characteristics and generation advancement; Indexing for Fon 1, Fon 2, anthracnose, powdery mildew, ZYMV resistance |

TABLE 1-continued

Chronological Description of the Development of Diploid Watermelon Variety SP-6

| Year | Season | Location | Cross | Progeny | Purpose |
|------|--------|----------|-------|---------|---------|
| 2011 | Winter | Khon Kaen, Thailand field; Woodland greenhouse | | BC1F6 | Selection for plant and fruit characteristics and generation advancement; Confirmation of Fon 2 and ZYMV resistance. |
| 2011 | Summer | Khon Kaen, Thailand field; Woodland greenhouse; Woodland field | | BC1F7 | Confirmation of plant and fruit characteristics and generation advancement; Confirmation Fon 1, Fon 2, anthracnose, powdery mildew, ZYMV resistance; Field observation and PVP data trial. Confirmation of line stability and phenotypic uniformity. |
| 2011 | Fall | Khon Kaen, Thailand field; Woodland greenhouse; Naples, FL field | | BC1F8 | Confirmation of plant and fruit characteristics and seed increase; Re-confirmation Fon 1, Fon 2, anthracnose, powdery mildew, ZYMV resistance; Field observation and PVP data trial. Re-confirmation of line stability and phenotypic uniformity. |

TABLE 2

Test of Resistance to Zucchini Yellow Mosaic Virus in SP-6 and Controls.

| Variety | Type | Species | Total Plant Inoculated | R | S | Results | Genotype |
|---------|------|---------|------------------------|---|---|---------|----------|
| SP-6 | Pollenizer | Citrullus lanatus var. lanatus | 22 | 20 | 2 | Resistant | RR |
| SP-5 | Pollenizer | Citrullus lanatus var. lanatus | 50 | 1 | 49 | Susceptible | SS |
| Dixielee | Control | Citrullus lanatus var. lanatus | 61 | 0 | 61 | Susceptible | SS |
| PI595203 | Control | Citrullus lanatus var. lanatus | 21 | 21 | 0 | Resistant | RR |

Standard Zucchini Yellow Mosaic Virus resistant test protocol was used for this test. The test was conducted in the pathology greenhouse of Woodland station and was finished in March 2011. "R"=resistant plants, "S"=susceptible plants. SP-6 is highly resistant to Zucchini Yellow Mosaic Virus based on pathology and molecular marker information. SP-5 is susceptible to Zucchini Yellow Mosaic Virus based on pathology and molecular marker information. Genotype data is based on molecular marker analysis (Ling et al (2009) Non synonymous single nucleotide polymorphisms in the watermelon eIF4E gene are closely associated with resistance to Zucchini yellow mosaic virus. TAG 120: 191-200). Table 3: Second Test of Resistance to Powdery Mildew in SP-5 and Controls.

TABLE 2

Second Test of Resistance to Zucchini Yellow Mosaic Virus in SP-6 and controls.

| Variety | Type | Species | Total Plant Inoculated | R | S | Results | Genotype |
|---------|------|---------|------------------------|---|---|---------|----------|
| SP-6 | Pollenizer | Citrullus lanatus var. lanatus | 25 | 25 | 0 | Resistant | RR |
| SP-5 | Pollenizer | Citrullus lanatus var. lanatus | 28 | 0 | 28 | Susceptible | SS |
| Dixielee | Control | Citrullus lanatus var. lanatus | 51 | 0 | 51 | Susceptible | SS |
| PI595203 | Control | Citrullus lanatus var. lanatus | 51 | 51 | 0 | Resistant | RR |

Standard Zucchini Yellow Mosaic Virus resistant test protocol was used for this test. The test was conducted in the pathology greenhouse of Woodland station and was finished on July 2011. "R"=resistant plants, "S"=susceptible plants. SP-6 is highly resistant to Zucchini Yellow Mosaic Virus based on pathology and molecular marker information. SP-5 is susceptible to Zucchini Yellow Mosaic Virus based on pathology and molecular marker information. Genotype data is based on molecular marker analysis (Ling et al (2009) Non synonymous single nucleotide polymorphisms in the watermelon eIF4E gene are closely associated with resistance to Zucchini yellow mosaic virus. TAG 120: 191-200).

SP-6 is also highly resistant to Powdery Mildew. Powdery mildew race is race 1 as revealed by melon differential host (McCreight, J. D. Melon-powdery mildew interactions reveal variation in melon cultigens and podosphaera xanthii races 1 and 2. J. Amer. Soc. Hort. Sci. 131(1):59-65. 2006).

SP-6 is highly resistant to anthracnose race 1 (Co 1) when Charleston Grey is used as the resistant check and Calhoun Grey is used as the susceptible check (Table 4).

SP-6 is intermediate resistant to Fon 2 while the susceptible control Black Diamond is susceptible to Fon 2 and resistant control PI296341-FR is intermediate resistant. Fusarium wilt race 2 is the most virulent race known. No resistance to this race is available in all commercial watermelon varieties. The resistance to Fon 2 is low even in the reported resistant source PI296341-FR (MARTYN RD, NETZER D. 1991. Resistance to races 0, 1, and 2 of Fusarium wilt of watermelon in Citrullus sp. PI 296341-FR. HortScience 26(4): 429-432). SP-6 has the best resistance to Fusarium wilt among the improved watermelons (Table 5).

SP-6 is highly resistant to Fusarium wilt race 1 (Fon 1) (Table 6).

The development of SP-6 maintained all the desirable traits of SP-5 by using SP-5 as the initial parent and then back-crossed the advanced lines to SP-5 (Table 1). The variety SP-6 has the same type of small leaf and deep leaf lobe. The fruit of SP-6 is also brittle and small, similar to the fruit of SP-5 (Table 7). The flowering and branching habits of SP-6 are the same of SP-6. The fruit phenotype of SP-6 is similar to the fruit of SP-5.

Diploid watermelon SP-6 was developed to be a pollenizer for triploid watermelon to produce seedless watermelon fruit. Because of the unique plant and fruit characteristics, much better resistance, and the broader genetic background, SP-6 is a superior pollenizer for seedless watermelon production. Seedless watermelon growers could produce solid seedless fruit using SP-6 as pollenizer, as commercial production has shown with SP-1, SP-4 and SP-5 as pollenizers in the United States, Mexico and Australia. Growers can get at least 25-33% more seedless fruit compared to what they are doing with standard diploid watermelon as pollenizer. Growers can freely select the best seedless varieties for their production programs when SP-6 is used as pollenizer because of its distinct fruit size, color and shape compared to commercial triploid watermelons. Using SP-6 as pollenizer growers can increase the yield potential of their triploid watermelon because of the simplified field management and prolonged flowering period of SP-6.

TABLE 4

Test of Resistance to Anthracnose in SP-6 and Controls.

| Variety | Type | Species | Isolate Used | Total Plant Inoculated | R | S | Results |
|---|---|---|---|---|---|---|---|
| SP-6 | Pollenizer | *Citrullus lanatus* var. *lanatus* | Col1 (6324) | 18 | 18 | 0 | Resistant |
| Charleston Grey | Standard Resistant Control | *Citrullus lanatus* var. *lanatus* | Col1 (6324) | 78 | 78 | 0 | Resistant |
| Calhoun Grey | Standard Susceptible Control | *Citrullus lanatus* var. *lanatus* | Col1 (6324) | 76 | 0 | 76 | Susceptible |

Standard anthracnose test was used for this test. The test was conducted in the pathology greenhouse of Woodland station and was finished in November, 2011.

TABLE 5

Test of Resistance to *Fusarium* wilt Race 2 in SP-6 and Controls.

| Variety | Type | Species | Isolate Used | Total Plant Inoculated | R | S | Results |
|---|---|---|---|---|---|---|---|
| SP-6 | Pollenizer | *Citrullus lanatus* var. *lanatus* | Race 2 (CalG) | 16 | 15 | 1 | Intermediate Resistant |
| PI296341FR | Standard Resistant Control | *Citrullus lanatus* var. *lanatus* | Race 2 (CalG) | 84 | 81 | 3 | Intermediate Resistant |
| Black Diamond | Standard Susceptible Control | *Citrullus lanatus* var. *lanatus* | Race 2 (CalG) | 86 | 12 | 74 | Susceptible |

Standard Fusarium wilt test protocol was used for this test. The test was conducted in the pathology greenhouse of Woodland station and was finished is November, 2011. "R"=resistant plants, "S"=susceptible plants.

TABLE 6

Test of Resistance to *Fusarium* wilt Race 1 in SP-5 and Controls.

| Variety | Type | Species | Isolate Used | Total Plant Inoculated | R | S | Results |
|---|---|---|---|---|---|---|---|
| SP-6 | Pollenizer | *Citrullus lanatus* var. *lanatus* | Race 1 (811B) | 18 | 18 | 0 | Resistant |
| Calhoun Grey | Standard Resistant Control | *Citrullus lanatus* var. *lanatus* | Race 1 (811B) | 63 | 60 | 3 | Resistant |
| Charleston Grey | Standard Susceptible Control | *Citrullus lanatus* var. *lanatus* | Race 1 (811B) | 60 | 7 | 53 | Susceptible |

Standard Fusarium wilt resistant test protocol was used for this test. The test was conducted in the pathology greenhouse of Woodland station and was finished in July, 2011. "R"=resistant plants, "S"=susceptible plants.

TABLE 7

Fruit Characteristics of SP-6 and Checks Grown at Woodland, CA Station in 2011 Summer (Woodland)

| Variety | Location** | Brix | Fruit Wt (kg) |
|---|---|---|---|
| SP-6 | Woodland | 5.7 +/− 0.5 | 1.4 +/− 0.3 |
| SP-5 | Woodland | 7.2 +/− 0.9 | 1.2 +/− 0.2 |
| SP-4 | Woodland | 6.9 +/− 0.6 | 2.0 +/− 0.3 |
| SP-1 | Woodland | 6.0 +/− 0.5 | 2.3 +/− 0.4 |
| Mickeylee | Woodland | 12.2 +/− 0.7 | 4.5 +/− 1.1 |

Watermelon SP-6 Characterstics

The following characteristics correspond to those provided on PVP Exhibit C.

Plant: Watermelon variety SP-6 is monoecious. Cotyledons of plants of watermelon variety SP-6 are flat. Typically, at first fruit set, there are approximately 7 main stems at crown per plant, and approximately 20 staminate and 8 pistillate flowers per plant. The stem of plants of watermelon variety SP-6 is round and pubescent, with a diameter of approximately 7 mm at second node. Typically, the inter-node length (cm) as expressed by the ratio of vine length (cm) by number of internodes (at last harvest) is approximately 9.

Leaf: The leaves of plants of watermelon variety SP-6, similar to those of SP-5, are significantly smaller with deep, non-overlapping leaf lobes and are more numerous than the variety Sangria™. The surface area of the leaf of plants of watermelon variety SP-6 is approximately 5 to 12 times less than the surface area of the typical diploid pollenizer, Sangria™ plant. The small, deeply lobed and non-overlapping leaves of plants of watermelon variety SP-6 allow more sunlight through to adjacent triploid watermelon plants. Leaves of watermelon variety SP-6 are ovate and longer than wide. The dorsal surface of the leaves is smooth and the ventral surface of the leaves is pubescent. The color of the leaves is dark green.

Branching: Plants of watermelon variety SP-6 are heavily branched (also referred to as "lacy vined"), having significantly more branches than the variety referred to as Sangria™. The lacy vine characteristic enables the pollenizer to produce more accessible male flowers, thereby enhancing exposure of the flowers to bees.

Fruit: The fruit rind of plants of watermelon variety SP-6 is very brittle and is easily broken. The brittle fruit rind splits easily, due to maturation or by breaking or splitting of the fruit during harvest of the seedless triploid watermelon. Splitting of fruit signals the plant that it hasn't completed its reproductive process inducing the plant to continue flowering for a longer period of time. Brittleness is conferred by a gene e (explosive rind, thin, and tender rind, bursting when cut (Rhodes & Dane, 1999, *Gene List for Watermelon*, Cucurbit Genetics Cooperative Report 22:71-77). The thickness of the rind is approximately 5 mm at the blossom end and approximately 5 mm at the sides of the fruit.

The size of mature fruits of plants of watermelon variety SP-6 is approximately 15 cm long and 14 cm wide (diameter at midsection). Small fruit size and brittleness were selected to decrease the load on the plant, thereby extending the duration of plant growth and flower production. Another advantage of the small fruit size is that it enables the harvester to easily distinguish the seedless fruit from seeded fruit, which is often difficult with most currently used pollenizers, which are selected based on their overall similarity to the seedless triploid plants. The primary color of the fruit is light green (Charleston Grey).

The flesh of the fruits of watermelon variety SP-6 is crisp, with fine-little fiber. Its color is yellow. In one embodiment, the percentage of soluble solids of juice taken from the center of the fruit is approximately 6% (compared to approximately 7% for variety SP-5). The fruits of watermelon variety SP-6 typically have no hollow heart, no placental separation and no transverse crack.

Flowering: The plants of watermelon variety SP-6 also flower approximately 7 to 10 days earlier than most diploid pollenizer plants currently used for the production of seedless watermelon, and continue flowering during fruit harvest time of the seedless watermelon, 2 to 3 weeks longer than most standard diploid pollenizer plants. Thus, the pollenizer plant of the invention has a flowering duration that is approximately 3 to 5 weeks longer than most pollenizers currently used. Staminate flowers have a width of approximately 3 cm (across the flower) and pistallate flowers have a width of approximately 4 cm (across the flower). The color of the flowers is yellow.

Seeds: Seeds of watermelon variety SP-6 are approximately 11 mm long, approximately 6.5 mm wide and approximately 2.3 mm thick. They are tan in color. 1,000 seeds of watermelon variety SP-6 weigh approximately 72 grams. There are approximately 600 seeds per fruit.

Other Traits: Watermelon variety SP-6 can be used either as donor of the set of traits disclosed above, or as the recurrent parent to develop additional pollenizer lines. These traits of are for example disease resistance (e.g. Gummy Stem Blight, Powdery Mildew, and Bacterial Fruit Blotch), insect resistance (e.g. cucumber beetle, aphids, white flies and mites), salt tolerance, cold tolerance and/or herbicide resistance added. These traits can be added to existing variety by using conventional backcrossing method, pedigree breeding method or genetic transformation. The methods of conventional watermelon breeding are taught in several reference books, e.g. Maynard, D. N. (editor), 2001, WATERMELONS Characteristics, Production and Marketing, ASHS Press; Mohr, H. C., Watermelon Breeding, in Mark J. Bassett (editor), 1986, Breeding Vegetable Crops, AVI Publishing Company, Inc. General methods of genetic transformation can be learned from publish references, e.g. Glich et al., (Eds), 1993, Methods in Plant Molecular Biology & Biotechnology, CRC Press.

Compared to the most similar variety SP-5, watermelon variety SP-6 is a new and very unique diploid watermelon for the following characteristic:

SP-6 is unique in that it has resistance to Zucchini Yellow Mosaic Virus (Tables 1-2).

SP-6 is unique compared to SP-5 as it has large seed size versus the small seed size of SP-5. SP-6 averages 14 seed per gram. SP-5 averages 67 seed per gram. SP-6 is unique compared to SP-5 as it has tan seed color versus the red seed color of SP-5 .

Method of Seedless Watermelon Production

Commercial seedless watermelon growers in NAFTA often use elongated diploid varieties with an Allsweet stripe pattern: light green skin with wide green stripes, as the pollenizer. The variety referred to as Sangria™ is one of the most preferred Allsweet type pollenizer and is available as a commercial product from Syngenta Seeds, Inc., Boise Id. Typically, the pollenizer is inter-planted with the triploid watermelon either between rows or within row. The current methods of planting diploid pollenizers often include planting the diploid plants at a distance from adjacent triploid such that they have the same field area available per plant as the field area that is available to the triploid watermelon plants. For example, currently watermelon growers may inter-plant the diploids within a row, whereby the space between all adjacent plants within the row are approximately equidistant.

Alternatively, diploid pollenizer plants are planted in separate rows between rows of triploid watermelon plants. All rows of diploid and triploid plants in such a field are planted approximately equidistant from each other. In other words, under current methods for producing seedless watermelon, the width of all diploid and triploid rows is often the same.

The method of the present invention includes planting plants of watermelon variety SP-6 in rows that are narrower than the triploid rows, thereby saving field area for production of triploid seedless watermelon.

EXAMPLE 1

Triploid watermelon plants are planted in parallel rows 7 feet apart and 3 feet apart within each row. However, plants of watermelon variety SP-6 are planted in a narrow row 3.5° wide (½ the width of the triploid rows) between every second and third triploid row. For example, rows A and B are two consecutive rows of triploids, each 7-foot wide. Row C is a diploid row that is 3.5 feet wide. Row D and E are the following two 7 foot wide rows of triploids, followed by the 3.5-foot wide row F of diploid plants. This pattern is repeated across the width of the field. Because the diploid row is narrower according to the method of the invention, the distance between rows B and D is 10.5 feet instead of a traditional distance of 14 feet. Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

EXAMPLE 2

Triploid watermelon plants are again planted in parallel rows 7 feet apart and 3 feet apart within each row. As in Example 1, plants of watermelon variety SP-6 are planted in a narrow row 3.5° wide, but are planted between every third and fourth triploid row. For example, rows A, B, and C, are three consecutive rows of triploids, each row being 7' wide. The following row D is a diploid row that is 3.5 feet wide. Row E, F, and G are the following three rows of triploids, all 7 feet wide, followed by a 3.5 foot wide row of plants of watermelon variety SP-6. This pattern is repeated across the width of the field. Because the diploid row is narrower according to the method of the invention, the distance between rows B and D is again 10.5 feet instead of a traditional distance of 14 feet. Using this ratio of 1 pollenizer row for every 3 triploid rows (1:3), 25% of the field would normally be used for the pollenizer plants. Reducing the width of the pollenizer row according to the method of the invention by one-half, the gain of space for planting additional triploid plants would be 25%/2 or approximately 12%.

EXAMPLE 3

Triploid watermelons are planted in parallel rows 8 feet apart and 3 feet apart within each row. Plants of watermelon variety SP-6 are planted in a narrow row 4.0 feet wide (½ the width of the triploid rows) between every second and third triploid row. For example, rows A and B are two consecutive rows of triploids, each 8 foot wide. Row C is a diploid row that is 4.0 feet wide. Row D and E are the following two 8 foot wide rows of triploids, followed by the 4.0 foot wide row F of diploid plants. This pattern is repeated across the width of the field. Because the diploid row is narrower according to the method of the invention, the distance between rows B and D is 12.0 feet instead of a traditional distance of 16 feet. Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

EXAMPLE 4

Referring to the above three examples, when triploids are planted in rows 8 feet apart, and the ratio of diploid to triploid is 1:3, it is now clear that the reduction of the pollenizer row width by one-half will gain space for planting additional 12%.

EXAMPLE 5

It is also within the scope of the invention to reduce the pollenizer row width to approximately ⅓ that of the triploid row width. Thus, according to the present invention, at any row width, when the ratio of diploid rows to triploid rows is:
(a.) 1:2, the savings of field area for additional triploid plants is (33%×⅔) or 22%.
(b) 1:3, the savings of field area for additional triploid plants is (25%×⅔) or 16.5%.
(c) 1:4, the savings of field area for additional triploid plants is (20%×⅔) or 13.2%.

It is also within the scope of the invention to reduce the pollenizer row width to approximately ⅔ that of the triploid row width.

EXAMPLE 6

It is also within the scope of the present invention to inter-plant the diploid plants within the rows of triploid plants. According to the invention, the triploid plants are first planted by machine or by hand in regularly spaced rows. The triploid plants within each row are planted, for example, 3 feet apart. After the triploid plants are in the field as described, the diploid pollenizer watermelon plants of the invention are inter-planted, by hand, within each row approximately midway between the triploid plants. When the transplant machine is properly set up, both the triploid plant and pollenizer plant can be transplanted at the same pass. Thus, in this example, the diploid plants are planted approximately 1.5 feet from the flanking triploid plants within the row. Due to the characteristics of watermelon variety SP-6, the diploid plants can be inter-planted within each row after every 2, 3, 4, 5, 6, 7, 8, 9, or 10 consecutive triploid plants. It is currently preferred in the industry to plant the diploid plants after every 2 (1:2) or 3 (1:3) triploid plants within the row. A 1:4 ratio has been reported, but is not normally used in commercial fields due to inadequate pollenization of the triploid plants. The field area saved under this example, when compared with both the current methods of planting diploids in separate rows or within a row at the ratios (diploid:triploid) of:
(a) 1:2, is 33.3%,
(b) 1:3, is 25%,
(c) 1:4, is 20%.

Methods of the present invention comprise planting plants of watermelon variety SP-6 in rows that are narrower than the rows containing the triploid plants. Although the narrower row will encourage growth of plants of watermelon variety SP-6 into the triploid plant row, the characteristics of watermelon variety SP-6 allow it maintain its ability to sufficiently pollinate the triploid plants in the field. Thus, watermelon variety SP-6 and method of the present invention increase the yield of seedless watermelon in a field.

In one aspect, a method of the present invention includes planting a plant of watermelon variety SP-6 within a row of triploid watermelon plants. In one embodiment, a method of the present invention includes planting a plant of watermelon variety SP-6 and a triploid watermelon plant in the same hole. In one embodiment, plants of watermelon variety SP-6 and triploid watermelon plants are planted in a ratio of 3-4:1, i.e. in every $3^{rd}$ or $4^{th}$ hole both a plant of watermelon variety SP-6 and a triploid watermelon plant are planted in the same hole. In one embodiment, a plant of watermelon variety SP-6 is planted within pollinating distance of a triploid watermelon plant.

In another aspect, a method of the present invention includes sowing a seed of watermelon variety SP-6 with a seed of triploid watermelon in the same cell of a seedling tray. In one aspect, a method of sowing watermelon seeds is provided, comprising the steps of (1) providing a mechanical seeder; and (2) using said mechanical seeder to seed a seedling tray with triploid seedless watermelon seed and SP-6 watermelon pollenizer seed. In a further aspect, the triploid seedless watermelon seed is planted in each cell of the seedling tray. In another aspect, the SP-6 watermelon pollenizer seed is planted into every 2nd, 3rd or 4th cell of the seedling tray. In another aspect, the ratio of triploid seedless watermelon seeds to SP-6 watermelon pollenizer seeds is 6:1, 5:1, 4:1, 3:1 or 2:1.

Production of Dihaploid Watermelon Plants

EXAMPLE 7

Anthers of watermelon plants are gamma-ray (produced by cobalt$^{60}$) irradiated for a dose of 0.4 KGy, or 0.3-0.6 KGy of soft X-rays. Irradiated pollen is gently transferred from the anthers to the receptive stigma on or before anthesis. Each ovary of the pollinated female receives an application of 50 ppm CPPU (a plant cytokinin growth regulator) to stimulate fruit development. Plants are monitored for pollination take and fruit development. Fruit is harvested 14 days or 21 days post-pollination.

Harvested immature fruit are carefully cut open under sterile conditions and the seeds are meticulously removed from the flesh. The distal portion of each seed is cut off before plating about 40 seeds to each plate of culture medium. Sealed plates with seeds are cultured at 25° C. with a 16-hour photoperiod in a culture room on a Murashige and Skoog Basal Medium, 30 g/L sucrose, 10 g/L agar supplemented either with 10 μM BA (2.25 mg/L) or 22.2 μM BA (5 mg/L) and 2.85 μM IAA (0.5 mg/L), pH 5.8 and dispensed into 100×15 petri dishes after autoclaving.

After 30 days, seeds are screened for greenish immature embryos for embryo rescue. Those with embryos are moved to fresh medium. As the embryos germinated and elongated, they are transferred to small culture jars with the same medium. When sufficient leaf tissue is present on the plantlet, a leaf is sampled and ploidy analysis is carried out measuring DNA content using flow cytometry (Zhang, Xingping, B. B. Rhodes and J. F. Whitesides, 1994. Determination of watermelon ploidy level using flow cytometry. Cucurbit Genetics Cooperative Rpt 17:102-105), or counting the number of chloroplast in guard cells (N. Sari et al., 1999, Comparison of ploidy level screening methods in watermelon: *Citrullus lanatus* (Thunb.) Matsum. and NakaiScientia, Horticulturae 82: 265±277).

Once the plantlets have been confirmed haploid, cuttings/clones are made and rooted in vitro. The medium consists of half strength MS basal salts, 20 g/L sucrose, 1.0 μM IBA (0.2 mg/L), 4 g/L agar and 1 g/L Phytagel, pH 5.8. Once a good root system has developed, plantlets are moved into the greenhouse and planted in trays. The chromosome doubling occurs in the greenhouse by applying 58 μM oryzalin (from product Surflan) to all apical and axillary nodes. Once plants are established and new flowers exhibit the presence of pollen confirming restored fertility, they are self-pollinated and seed is harvested. Further increase can be done in a field isolated from any other watermelon plant, or physically isolated in a net cage. The chromosome doubling process can also be conducted tissue cultures stage (Zhang, Xingping, B. B. Rhodes, H. T. Skorupska and W. Bridges, 1995. Generating tetraploid watermelons using colchincine in vitro. In G. E. Lester and J. R. Dunlap (eds) Cucurbitaceae '94 p144-147. Gateway Printing, Edinburg, Tex.).

DEPOSIT

Applicants have made a deposit of at least 2500 seeds of watermelon variety SP-6 with the American Type Culture Collection (ATCC), Manassas, Va., 20110-2209 U.S.A., ATCC Deposit No: PTA-12691. This deposit of watermelon variety SP-6 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant watermelon line and the like may be practiced within the scope of the invention, as limited only by the scope of the appended claims. Thus, although the foregoing invention has been described in some detail in this document, it will be obvious that changes and modification may be practiced within the scope of the invention, as limited only by the scope of the appended claims.

All references are incorporated herein in their entities.

What is claimed is:

1. Seed of diploid watermelon variety SP-6, wherein representative seed of said variety is having been deposited under ATCC Accession No: PTA-12691.

2. A diploid plant of watermelon variety SP-6, wherein representative seed of said variety is having been deposited under ATCC Accession No: PTA-12691.

3. Pollen of the plant of claim 2.

4. An ovule of the plant of claim 2.

5. Fruit of the plant of claim 2, wherein the fruit is produced by self-pollination of the plant.

6. A method for producing triploid, seedless watermelon fruit, wherein the method comprises the steps of:
    a) planting a field with rows of triploid watermelon plants;
    b) inter-planting a diploid watermelon plant according to claim 2 within said rows of triploid watermelon plants after every 2nd, 3rd, 4th, 5th, 6th, 7th, 8th, 9th, or 10th triploid plants;
    c) allowing pollination of said triploid watermelon plants by pollen of said diploid watermelon plant to obtain triploid, seedless watermelon fruit; and
    d) harvesting said triploid, seedless watermelon fruit.

7. A method for producing triploid, seedless watermelon fruit, wherein the method comprises the steps of:
    a) planting a field with rows of triploid watermelon plants;
    b) planting said field with rows of diploid watermelon plants according to claim 2, wherein the rows of diploid watermelon plants are approximately one-third to two-thirds the width of the rows of triploid watermelon plants; and
    c) allowing pollination of said triploid watermelon plants by pollen of said diploid watermelon plants to obtain triploid, seedless watermelon fruit.

8. The method for producing triploid, seedless watermelon fruit according to claim 7, wherein the rows of diploid watermelon plants are approximately one-half to two-thirds the width of the rows of triploid watermelon plants.

9. The method for producing triploid, seedless watermelon fruit according to claim 7, wherein said rows of diploid watermelon plants are planted after every two rows of triploid watermelon plants.

10. The method for producing triploid, seedless watermelon fruit according to claim 7, wherein said rows of diploid watermelon plants are planted after every three rows of triploid watermelon plants.

11. The method for producing triploid, seedless watermelon fruit according to claim 7, wherein said rows of diploid watermelon plants are planted every four rows of triploid watermelon plants.

12. The method for producing triploid, seedless watermelon fruit according to claim 7, further comprising harvesting said triploid, seedless watermelon fruit.

13. The method for producing triploid, seedless watermelon fruit according to claim 7, wherein the rows of diploid watermelon plants are approximately one-third to one-half the width of the rows of triploid watermelon plants.

14. A method of increasing the yield of triploid, seedless watermelon plants, wherein the method comprises the steps of:
   a) obtaining the diploid watermelon plants according to claim 2 for pollenizing said triploid, seedless watermelon plants;
   b) planting said diploid watermelon plants in a field of triploid watermelon plants;
   c) allowing pollination of said triploid watermelon plants by pollen of said diploid watermelon plants to obtain triploid, seedless watermelon fruit; and
   d) harvesting said triploid, seedless watermelon fruit.

15. The method of increasing the yield of triploid, seedless watermelon plants according to claim 14, wherein planting of said diploid watermelon plants is at a ratio of approximately equal to or less than 1 diploid watermelon plant to 2 triploid, seedless watermelon plants.

16. The method of increasing the yield of triploid, seedless watermelon plants according to claim 14, wherein planting of said diploid watermelon plants is at a ratio of approximately equal to or less than 1 diploid watermelon plant to 4 triploid, seedless watermelon plants.

17. A method for producing seeds of a watermelon plant, wherein the method comprises the steps of:
   a) growing in a field the watermelon plant according to claim 2;
   b) conducting pollination of said plant; and
   c) harvesting seed of said plant.

18. The method according to claim 17, further comprising drying said seed.

19. A method for producing a hybrid watermelon variety, wherein the method comprises the steps of:
   a) planting in a field a first and a second watermelon plant, wherein said first watermelon plant is the male parent, wherein said second watermelon plant is the female parent, and wherein said first or said second watermelon plant is the watermelon plant according to claim 2;
   b) conducting pollination between said first and second watermelon plants; and
   c) harvesting seed from said female parent, wherein said seed is seed of a hybrid watermelon variety.

20. A method for producing triploid, seedless watermelon fruit, wherein the method comprises the steps of:
   a) interplanting a diploid watermelon plant according to claim 2 and triploid watermelon plants in a field; and
   b) allowing pollination of said triploid watermelon plants by pollen of said diploid watermelon plant to obtain triploid, seedless watermelon fruit.

21. The method for producing triploid, seedless watermelon fruit according to claim 20, further comprising harvesting said triploid, seedless watermelon fruit.

22. A method for producing triploid, seedless watermelon fruit, wherein the method comprises the steps of:
   a) interplanting seed of a diploid watermelon variety according to claim 1 and triploid watermelon plants in a field;
   b) allowing said seed to grow into diploid watermelon plants; and
   c) allowing pollination of said triploid watermelon plants by pollen of said diploid watermelon plants to obtain triploid, seedless watermelon fruit.

23. A method for producing triploid, seedless watermelon fruit, wherein the method comprises the steps of:
   a) interplanting diploid watermelon plants according to claim 2 and seed of triploid watermelon plants in said field;
   b) allowing said seed to grow into triploid watermelon plants; and
   c) allowing pollination of said triploid watermelon plants by pollen of said diploid watermelon plants to obtain triploid, seedless watermelon fruit.

24. A method for producing triploid, seedless watermelon fruit, wherein the method comprises the steps of:
   a) interplanting seed of a diploid watermelon variety according to claim 1 and seed of triploid watermelon plants in a field;
   b) allowing said seed to grow into diploid watermelon plants and triploid watermelon plants, respectively; and
   c) allowing pollination of said triploid watermelon plants by pollen of said diploid watermelon plants to obtain triploid, seedless watermelon fruit.

25. A method of sowing watermelon seeds, comprising:
   a) providing a mechanical seeder; and
   b) using said mechanical seeder to seed a seeding tray with triploid watermelon seed and the seed of claim 1.

26. The method of claim 25, wherein the triploid watermelon seeds are seeded in each cell of the seedling tray.

27. The method of claim 25, wherein the seeds of claim 1 are planted in every 2nd, every 3rd, every 4th or every 5th cell of the seeding tray.

28. The method of claim 25, wherein the triploid watermelon seed and seed of claim 1 are planted in a ratio of 6:1, 5:1, 4:1, 3:1 or 2:1, respectively.

29. A method of producing a grafted watermelon plant comprising grafting a watermelon scion onto a suitable rootstock, wherein the plant of claim 2 is used as the scion.

* * * * *